United States Patent [19]

Husted et al.

[11] Patent Number: 4,777,135
[45] Date of Patent: Oct. 11, 1988

[54] METHOD FOR PRODUCING BUTANOL BY FERMENTATION

[75] Inventors: Gary R. Husted, Shelburne, Vt.; Joseph D. Santangelo, Cape Town, South Africa; Dunbar W. Bostwick, Shelburne, Vt.

[73] Assignee: The University of Vermont and State Agricultural College, Burlington, Vt.

[21] Appl. No.: 697,778

[22] Filed: Feb. 4, 1985

[51] Int. Cl.$^4$ .................................................. C12P 7/16
[52] U.S. Cl. .................................. 435/160; 435/150; 435/152; 435/154; 435/161; 435/244; 435/253; 435/842
[58] Field of Search ............... 435/160, 150, 152, 253, 435/161, 842, 244, 253, 154

[56] References Cited

U.S. PATENT DOCUMENTS 4,105,498 8/1978 Hertl et al. ........................ 435/260
4,424,275 1/1984 Levy ................................... 435/813

OTHER PUBLICATIONS

Van Auken et al., "Comparison of the Effects of Three Fluoro Carbons on Certain Bacteria", *Can. J. Microbiol.*, vol. 21, pp. 221–226, 1975.

*Primary Examiner*—Charles F. Warren
*Assistant Examiner*—Irene Marx
*Attorney, Agent, or Firm*—Foley & Lardner, Schwartz, Jeffery, Schwaab, Mack, Blumenthal & Evans

[57] ABSTRACT

A method for producing butanol by fermentation is provided. The method is carried out by culturing a butanol-producing microorganism in a culture medium containing a fluorocarbon selected from the group consisting of monofluorotrichloromethane, monofluorodichloromethane, monochloroheptafluoroethane, dichlorodifluoromethane, dichlorotetrafluoroethane and mixtures thereof in an amount sufficient to increase butanol production, and by separating the butanol from the culture medium.

14 Claims, 2 Drawing Sheets

The effect of various concentrations of Freon-11 added to the culture medium (PYG) on cell growth, measured as absorbance at 660 nm o = No Freon-11 added   △ = 0.5g/l of Freon-11 added
● = 0.1g/l of Freon-11 added   X = 1.0g/l of Freon-11 added

METHOD FOR PRODUCING BUTANOL BY FERMENTATION

BACKGROUND OF THE INVENTION

This invention relates to a new and improved method for producing butanol by fermentation. In particular, the invention relates to a method for producing butanol by fermentation by culturing a butanol-producing microorganism in a culture medium containing a fluorocarbon, and separating the butanol from the culture medium.

For many years, butanol was almost exclusively produced in commercial quantities in acetone, butanol, ethanol (ABE) fermentation processes. However, abundant supplies of fossil fuels and breakthroughs in catalysis ultimately led to the relinquishment of butanol fermentation on a commercial basis. Since the advent of the recent oil shortage, there has been renewed interest in producing butanol by the fermentation of renewable resources.

Butanol either in its isomeric forms (normal, secondary and tertiary) or as its methyl ether can be blended with methanol to extend fuel supplies and increase the octane of fuel blends. Butanol also can act as a cosolvent for diesel fuel, ethanol and vegetable oils.

In a conventional butanol fermentation, a butanol producing microorganism is grown in a culture medium containing about 6% weight/volume of carbohydrates to produce about 4% weight/volume of solvents, namely acetone, butanol and ethanol. This translates into approximately 2.4% weight/volume butanol, 1.2% weight/volume acetone and 0.4% weight/volume ethanol. Thus, one of the problems associated with conventional butanol fermentation is a dilute aqueous product stream.

It is known that butanol like many other types of alcohols is toxic above certain concentration levels to microorganisms. Since a concentration of as little as 3% weight/volume butanol may be toxic to the microorganisms, the fermentation must be carried out in a manner so that the toxic effects of the butanol are minimized.

Accordingly, it is an object of the present invention to provide a new and improved method for increasing the production rate of butanol and increasing the final concentration of butanol.

It is also an object of this invention to provide a method for stimulating the growth rate of microorganisms of the genus Clostridium.

SUMMARY OF THE INVENTION

These and other objects of the invention are accomplished by culturing a butanol-producing microorganism in a culture medium containing a fluorocarbon selected from the group consisting of monofluorotrichloromethane, monofluorodichloromethane, monochlorodifluoromethane, dichlorodifluoromethane, dichlorotetrafluoroethane and mixtures thereof in an amount sufficient to increase butanol production, and separating the butanol from the culture medium.

It has been found that the addition of a suitable fluorocarbon to the culture medium increases the production rate of butanol by as much as about 20% and increases the final concentration of butanol by as much as about 12%. The production of butanol using the fluorocarbons of the invention is a relatively inexpensive process, as compared to known production techniques, because the product stream is more concentrated.

BRIEF DESCRIPTION OF THE DRAWINGS

FIG. 1-B is a graph which shows the growth characteristics of *C. acetobutylicum* grown in PYG medium containing 1.0 g/l of Freon-11.

DESCRIPTION OF THE PREFERRED EMBODIMENTS

Figure 1:
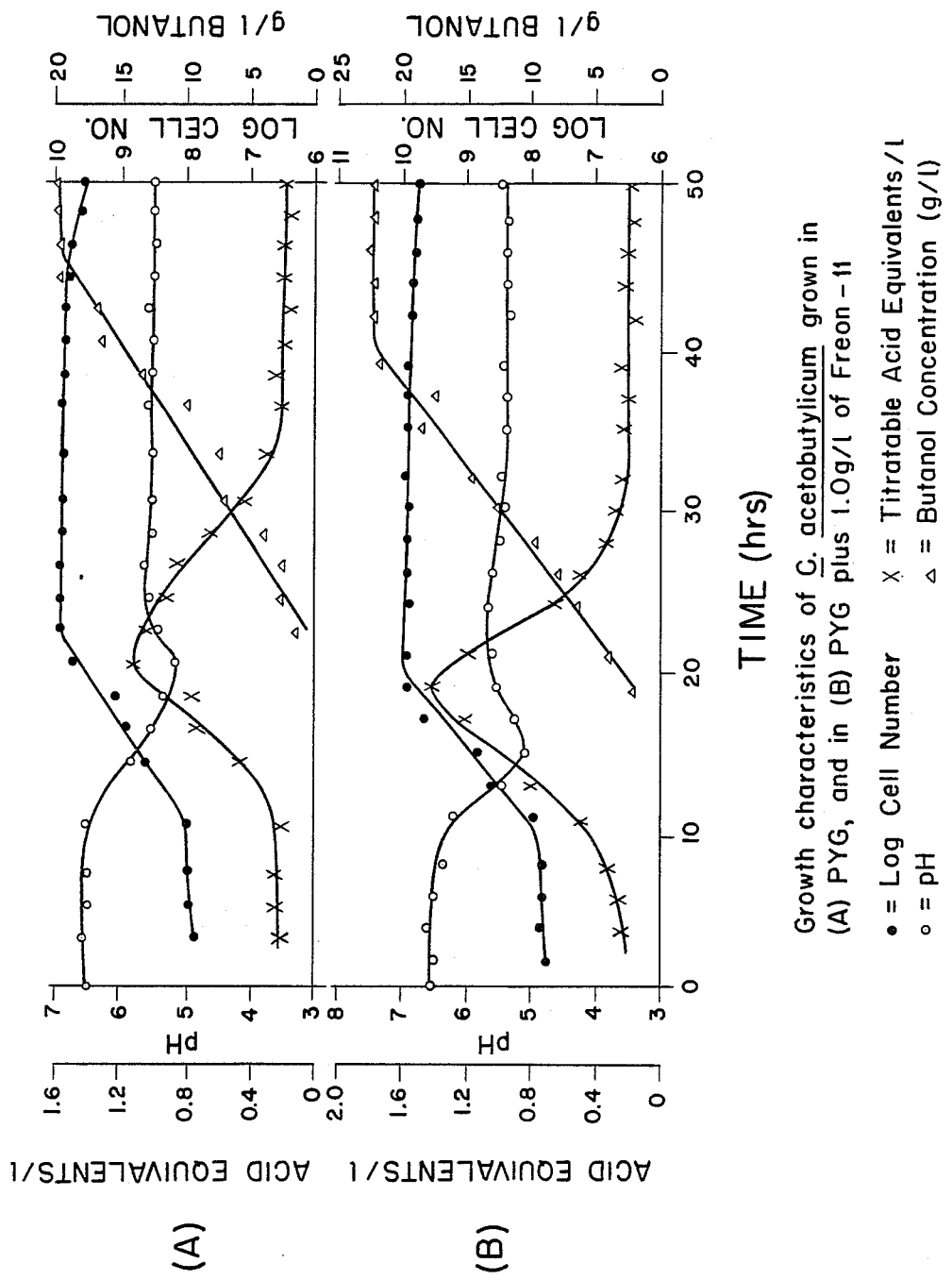
FIG. 1-A is a graph which shows the growth characteristics of *C. acetobutylicum* grown in PYG medium.

The microorganisms considered suitable for use in this invention are butanol-producing microorganisms including microorganisms of the genus Clostridium. The Clostridium are characterized as strictly anaerobic, gram positive spore forming rods. They can be isolated from many natural sources including soil, corn and potatoes. The preferred species of Clostridium is *Clostridium acetobutylicum*. It readily ferments carbohydrates to acetic and butyric acid intermediates, whereupon these intermediates are converted to the neutral end products acetone, butanol and ethanol.

A culture of *Clostridium acetobutylicum* is American Type Culture Collection (A.T.C.C.) accession No. 824. This culture provides reproducible fermentation characteristics and produces commercial yields of butanol, acetone and ethanol in a ratio of 6:3:1, respectively. The fermentation of this culture in a culture medium containing 6% weight/volume of carbohydrates results in about 4% weight/volume of total solvents. This translates into approximately 2.4% w/v butanol, 1.2% w/v acetone and 0.4% w/v ethanol.

The culture medium considered suitable for use in this invention contains substances to promote the growth of butanol-producing microorganisms. Representative substances include a substrate plus other materials like amino acids, enzymes and vitamins. While sugar or starch raw materials may be used as substrates, the butanol-producing microorganism may ferment pentoses, enabling good yields of butanol from hydrolysates of pentose-rich feedstocks such as agricultural crop residues, bagasse and deciduous woods such as poplar and willow. A preferred culture medium, known as PYG, consists of 2% weight/volume bacto-peptone (Difco Laboratories, Detroit, Michigan), 1% weight/volume yeast extract (Difco Laboratories) and 6% weight/volume glucose (Sigma Chemical, St. Louis, Missouri) dissolved in distilled water.

The fluorocarbons considered suitable for use in this invention are selected from the group consisting of monofluorotrichloromethane, monofluorodichloromethane, monochlorodifluoromethane, dichlorodifluoromethane, dichlorotetrafluoroethane and mixtures thereof. A preferred fluorocarbon is monofluorotrichloromethane such as the material sold by E.I. DuPont de Nemours Co. Inc. of Wilmington, Del. under the trade name Freon-11.

The amount of fluorocarbons employed in accordance with the invention ranges from about 0.01 g/l to 10.0 g/l. The amount of the monofluorotrichloromethane employed ranges from about 0.1 g/l to 1.0 g/l, with about 1.0 g/l being preferred. The solubility of monofluorotrichloromethane in water at 37° C. is approximately 1.0 g/l.

Butanol may be separated from the fermentation liquor by a number of established procedures including distillation, freezing techniques or solvent extraction. Typically, the separation of butanol from the fermentation liquor is accomplished by solvent extraction using a fluorocarbon like monofluorotrichloromethane followed by vacuum evaporation as set forth in U.S. Pat. No. 4,260,836, which disclosure is hereby incorporated by reference.

In an embodiment of the invention, continuous culture techniques either with immobilized or with free floating microorganisms may be employed to increase the rate of butanol production and to increase the concentration of butanol in the fermentation liquor. Once the butanol is separated from the fermentation liquor, the remaining material may be blended with fresh substrate and then recycled back into the fermentation. This recycling stimulates the production of butanol at a higher rate, lowers the recovery costs and avoids butanol toxicity problems.

The following examples further illustrate the present invention but are not intended to limit its scope in any way.

EXAMPLE 1

This example illustrates the growth characteristics of *Clostridium acetobutylicum* grown in PYG medium as well as in PYG medium containing 1.0 g/l of monofluorotrichloromethane.

2800 ml of PYG medium were prepared by mixing 2% w/v bacto-peptone (Difco Laboratories), 1% w/v yeast extract (Difco Laboratories) and 6% w/v glucose (Sigma Chemical) in distilled water. The medium was prereduced by purging with filtered prepurified nitrogen for a minimum of 24 hours using a Balston Microfibre filter tube (grade AQ) (Balston Inc., Lexington, Mass.). 1.4 g of a monofluorotrichloromethane sold by E.I. DuPont de Nemours Co. Inc. under the tradename Freon-11 were added to 1400 ml of the prereduced PYG medium. Freon-11 was stored and measured by weight in the cold.

A 0.2 ml inoculum was removed from 200 ml of an exponential phase culture of *Clostridium acetobutylicum*, A.T.C.C. strain No. 824, grown in PYG medium described above. This inoculum was adjusted to give an initial cell density of $1 \times 10^7$ cells/ml by direct count.

About 0.1 ml of the adjusted inoculum, representing about $1 \times 10^6$ cells, was added to 1400 ml of PYG medium and to 1400 ml of PYG medium containing 1.0 g/l of Freon-11. The pH of the cultures at the commencement of the study was 6.5. The cultures were incubated in a Bio-Flo-Fermentor (New Brunswick Scientific, New Brunswick, N.J.) at 37° C. for 50 hours.

1 ml aliquots were withdrawn periodically from the cultures to determine the log cell number, pH, tritratable acid equivalents/l and butanol concentration in g/l and to observe the morphology changes of the *C. acetobutylicum*.

The optical density of the cultures was measured as absorbance, at 660 nm using a Coleman Junior spectrophotometer (Perkin Elmer Company, Maywood, Ill.) against a blank of sterile PYG.

The acetone, n-butanol and ethanol were assayed by means of gas chromatography, using a 6% FFAP (Varian Instruments Inc., Burlington, Mass.) on Porapak Q (Waters Associates Inc., Milford, Mass.) (80/100 mesh) - 182.88 cm (6 ft) by 31.75 mm (⅛ in) stainless steel column (Supelco, Bellafonte, Pa.), as described by Bricknell et al. in *Anal. Biochem.*, Vol. 51, pages 23–31 (1973), on a Perkin Elmer 900 gas chromatograph equipped with a flame ionization detector (Perkin Elmer Co., Norwalk, Conn.). The injector, column oven and detector temperatures are 215° C., 200° C. and 230° C., respectively. The carrier gas was helium, with a flow rate of 30 ml/min. The hydrogen used for the detector was set at 25 ml/min. Acids were assayed by titration with 0.02N NaOH, using phenolphthalein as an end point indicator.

All microscopic examinations were performed using a Leitz Labolux microscope equipped with phase contrast optics after Zernike (Ernst Leitz Inc., Rockleigh, N.J.). Bacterial counts were carried out using a Petroff-Hausser bacteria counter (C. A. Hausser & Son, Philadelphia, Pa.). Encapsulation was determined by negative staining with India ink. Granulose presence was determined by staining with iodine.

Referring to FIG. 1-A, microscopic observations of lag phase samples withdrawn from the culture vessel during the first 9 hours of fermentation revealed phase-dark, long rods, in pairs that generally lack motility. After about 9 to 11 hours from the commencement of the study, the cells were predominantly phase dark rods which were highly motile and occurred singly. During this time, the pH value of the medium dropped as the quantity of titratable acids (n-butyric and acetic) rose, and the population growth rate began to increase.

The period of 10 to 22 hours after the commencement of the study represented the period of exponential growth with a doubling time of 109 minutes, i.e. a cell generation time ($T_g$) of 0.55 generations/hr. During this acidogenic stage the cells remained phase dark and were highly motile. The pH value dropped until it reached a break point of 5.20 at 20 hours. The amount of titratable acids increased, and peaked at 1.12 equivalents/l concurrent with the pH break point. At this point the dark rods began to exhibit a decrease in motility and iodine staining revealed granulose particles in the cells.

The solvogenic phase occurred between 22 and 44 hours. The pH increased until it reached a constant value of 5.5. Concurrently, the concentration of acetic and butyric acids dropped. Cell morphology then changed from phase dark rods to phase bright clostridial cells. Butanol was first detected at 22 hours. It was produced at a rate of approximately 0.8 g/l-hour. When cell division reached an equilibrium with cell death, a plateau on the growth curve was observed.

Referring to FIG. 1-B, the initial parameters of this culture were identical to those described above and shown in FIG. 1-A. A lag phase was again seen from 0 to 9 hours, followed by an exponential or acidogenic phase of growth from 10 to 22 hours. The pH value of the culture began to drop at 9 hours, but the rate of decreae was more rapid than in the control. The pH break point acids was seen at 16 hours. The pH reached a lower value at the break point (5.05) as compared to the control (5.20). The rate of acid production was more rapid than in the control, and the concentration of titratable acids peaked at a higher value (1.42 equivalents/l at 19 hours).

The population doubling time ($T_{pd}$) is less in the culture containing Freon-11 as compared to the control. The population doubling time between 10 and 22 hours was 85 minutes ($T_g = 0.71$ generations/hr) as deemed from the fitted regression line of the values.

At 20 hours following inoculation, the onset of the solvogenic phase was accompanied by a predominance of clostridial cells. The cell population density reached at 20 hours was $8.27 \times 10^9$ cells/ml, which was greater than the level reached in the control fermentation. The pH value of both cultures remained constant at 5.4 throughout the solvogenic phase. The amount of titratable acids declined steadily from this point on. Butanol was first observed at 18 hours which is earlier than in the control. The rate of butanol production was determined to be 0.98 g/l per hour, and this rate was higher than the results for the control fermentation. The butanol level continued to rise until 40 hours, at which time the rate of production began to decrease. The final concentrations of butanol, acetone and ethanol after 50 hours were 22.53 g/l, 11.13 g/l and 3.77 g/l respectively, yielding a total solvent concentration of 37.43 g/l while the final concentrations of butanol, acetone and ethanol in the control were 20.02 g/l, 10.43 g/l and 3.39 g/l respectively, yielding a total solvent concentration of 33.84 g/l.

EXAMPLE 2

This example illustrates the effect of various concentrations of Freon-11 on the concentration of butanol obtained in the fermentation broth.

1200 ml of PYG medium was prepared as described in Example 1, except that the medium was prereduced by placing it onto a gyratory shaker overnight in an anaerobic chamber (Coy Laboratory Products, Ann Arbor, Mich.) containing 10% hydrogen and 5% carbon dioxide in nitrogen. The PYG medium was distributed equally among four 300 ml sidearm flasks. One 300 ml sidearm flask served as the control culture. The three remaining flasks contained Freon-11 in concentrations of 0.1 g/l, 0.5 g/l and 1.0 g/l, respectively.

A 0.2 ml inoculum was removed from an exponential phase culture of *Clostridium acetobutylicum*, A.T.C.C. strain No. 824, grown in PYG medium prepared as described in Example 1. This inoculum was adjusted to give an initial cell density of $1 \times 10^7$ cells/ml by direct count. About 0.1 ml of the adjusted inoculum, representing about $1 \times 10^6$ cells, was added to each of the four 300 ml sidearm flasks. The cultures were incubated in the anaerobic chamber at 37° C. for 40 hours. The cell growth of the four cultures, measured as absorbance at 660 nm, is graphically depicted in FIG. 2.

Figure 2:
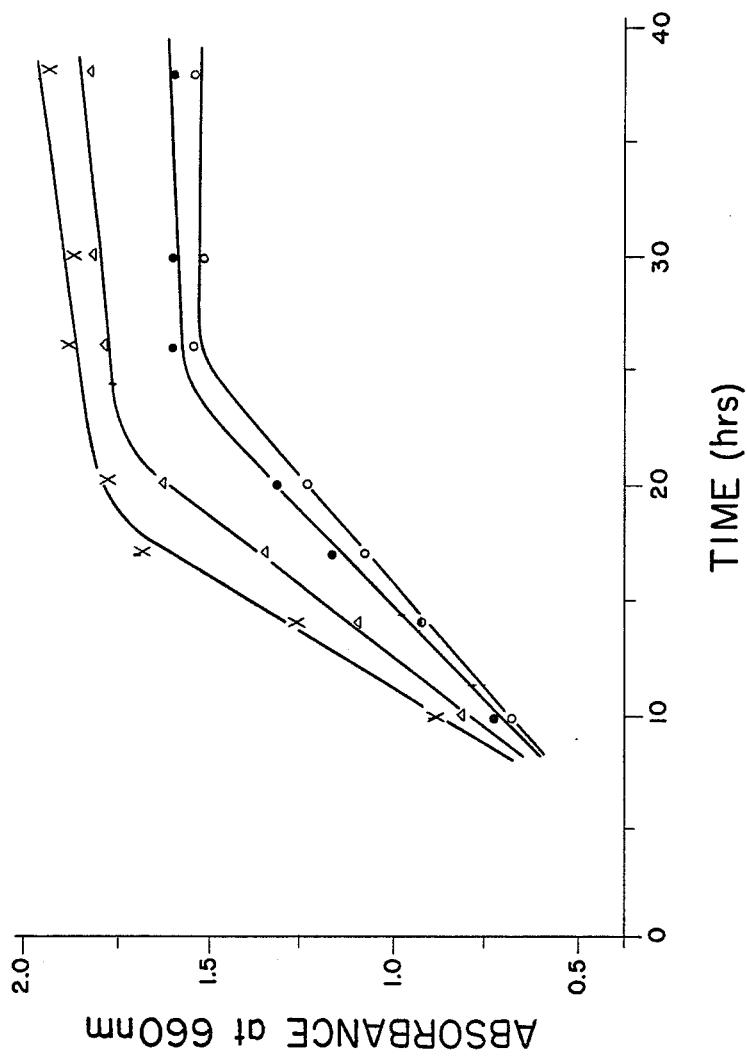
FIG. 2 is a graph which shows the effects of various concentrations of Freon-11 on cell growth.

Referring to FIG. 2, Freon-11 was the most effective at a level of 1.0 g/l in increasing cell growth. While the final butanol concentration reached in the control was 19.7 g/l, the final butanol concentration in the culture containing 1.0 g/l Freon-11 was 22.1 g/l. This represented an increase in butanol of about 12%. Acetone and ethanol levels did not show an increase over the controls.

EXAMPLE 3

This example gives the results of a statistical analysis of cell growth with 1.0 g/l Freon-11 as compared with the same medium without Freon-11, and further demonstrates the improvement in butanol production rate and final butanol concentration obtained in accordance with this invention.

Cultures of *Clostridium acetobutylicum* were prepared in each of 20 300 ml sidearm flasks as described in Example 2. Freon-11 was added to 10 of the cultures prior to inoculation to give a concentration of 1.0 g/l. The remaining 10 cultures served as controls. The cultures were incubated in an anaerobic chamber under conditions described in Example 2 and the cultures were monitored for their cell generation times, rates of butanol production and final concentrations of butanol. The procedures for determining these values are set forth in Example 1.

Table 1 shows the resulting generation times, butanol production rates and final butanol concentrations for these cultures. Table II shows some statistical calculations derived from these data, which were determined to be normally distributed by using Bartlett's test for homogeneity of variance, as described by Snedecor et al. in *Statistical Methods*, pp. 255–273 (1980). This allows the use of analysis of variance (ANOV) techniques, as described by Snedecor et al. in *Statistical Methods*, pp. 215–237 (1980), to determine whether a significant difference exists between the control and treated cultures. Table III shows the final ANOV comparison.

Based upon the data shown in Tables I, II and III it is concluded that a significant difference exists between the generation times, rates of butanol production and final concentrations of butanol between the cultures with 1.0 g/l Freon-11 and without Freon-11. The increase in mean generation time was about 29%, the increase in the mean butanol production rate was about 19% and the increase in the mean final butanol concentration was about 12%.

No significant difference was demonstrated for production rates and final concentrations of acetone or ethanol, using the same techniques.

TABLE I

RESULTS FROM THE GROWTH ANALYSIS EXPERIMENT

| | (A) GENERATION TIME | | (B) BUTANOL g/l-hour | | (C) [BUTANOL] g/l | |
|---|---|---|---|---|---|---|
| SAMPLE | CON | F-11 | CON | F-11 | CON | F-11 |
| 1 | 0.5024 | 0.7237 | 0.7867 | 0.9154 | 19.21 | 22.04 |
| 2 | 0.5616 | 0.7011 | 0.8132 | 0.9666 | 19.89 | 21.97 |
| 3 | 0.6007 | 0.6892 | 0.7557 | 0.9792 | 19.33 | 22.54 |
| 4 | 0.5134 | 0.7336 | 0.8096 | 0.9891 | 19.73 | 22.16 |
| 5 | 0.5597 | 0.7719 | 0.8201 | 0.9225 | 20.04 | 22.80 |
| 6 | 0.5335 | 0.7632 | 0.8191 | 0.9013 | 19.02 | 21.83 |
| 7 | 0.5571 | 0.6747 | 0.8781 | 0.9732 | 20.82 | 22.01 |
| 8 | 0.6021 | 0.7152 | 0.7232 | 0.9563 | 19.11 | 21.84 |
| 9 | 0.5876 | 0.7406 | 0.8063 | 0.9921 | 19.64 | 22.63 |
| 10 | 0.5779 | 0.7313 | 0.8112 | 0.9813 | 19.85 | 22.59 |

Results of the growth analysis experiment. CON = cultures grown in PYG, F-11 = cultures grown in PYG plus 1.0 g/l of Freon-11.

TABLE II

STATISTICS CALCULATED FOR GROWTH ANALYSIS

| | (A) GENERATION TIME | | (B) BUTANOL g/l-hour | | (C) [BUTANOL] g/l | |
|---|---|---|---|---|---|---|
| | CON | F-11 | CON | F-11 | CON | F-11 |
| $\Sigma Y$ | 5.5951 | 7.2345 | 8.0332 | 9.5770 | 196.64 | 222.41 |
| $\Sigma Y^2$ | 3.1412 | 5.2422 | 6.4683 | 9.1816 | 3869.34 | 4947.80 |
| $\overline{Y}$ | 0.5595 | 0.7235 | 0.8033 | 0.9577 | 19.66 | 22.24 |
| $\Sigma y^2$ | 0.0106 | 0.0084 | 0.0151 | 0.0097 | 2.61 | 1.18 |
| s | 0.0344 | 0.0306 | 0.0409 | 0.0329 | 0.54 | 0.36 |

Growth analysis experiment statistics calculated from the data found in Table I. $\Sigma Y$ = the sum the individual values; $\Sigma Y^2$ = the sum of each squared value; $\overline{Y}$ = the mean value group; $\Sigma y^2$ =0 the sum of squares; s = the standard deviation. CON = cultures grown in PYG; F-11 = cultures grown in PYG plus 1.0 g/l of Freon-11.

TABLE III

| FINAL ANOV FOR GROWTH ANALYSIS | | | | |
|---|---|---|---|---|
| VS | DOF | $\Sigma y^2$ | MS | F |
| (A) Between Groups | 1 | 0.1344 | 0.1344 | 122.18** |
| Residual | 18 | 0.0191 | 0.0011 | |
| $\Sigma$ | 19 | 0.1535 | | |
| (B) Between Groups | 1 | 0.1192 | 0.1192 | 86.59** |
| Residual | 18 | 0.0247 | 0.0014 | |
| $\Sigma$ | 19 | 0.1439 | | |
| (C) Between Groups | 1 | 33.20 | 33.20 | 157.87** |
| Residual | 18 | 3.79 | 0.21 | |
| $\Sigma$ | 19 | 36.99 | | |

Final ANOV results and calculations for the growth analysis experiments. VS = variation source; DOF = degrees of freedom; $\Sigma y^2$ = sum of squares; MS = mean square (variance); F = variance ratio; ** = significance demonstrated at a 99% confidence level (ie: $p < 0.01$).
(A) - Final ANOV for comparison of generation times
(B) - Final ANOV for comparison of butanol production rates
(C) - Final ANOV for comparison of butanol yields

We claim:

1. A method for producing butanol by fermentation which comprises culturing under anaerobic conditions a butanol-producing microorganism in a culture medium containing a fluorocarbon selected from the group consisting of monofluorotrichloromethane, monofluorodichloromethane, monochlorodifluoromethane, dichlorodifluoromethane, dichlorotetrafluoroethane and mixtures thereof in an amount sufficient to increase butanol production, and separating the butanol from the culture medium.

2. A method according to claim 1, wherein the microorganism is of the genus Clostridium.

3. A method according to claim 2, wherein the microorganism is *Clostridium acetobutylicum*.

4. A method according to claim 3, wherein the microorganism is American Type Culture Collection accession No. 824.

5. A method according to claim 1, wherein the fluorocarbon is added in an amount of about 0.01 g/l to 10.0 g/l.

6. A method according to claim 1, wherein the fluorocarbon is monofluorotrichloromethane.

7. A method according to claim 6, wherein the monofluorotrichloromethane is added in an amount of about 0.1 g/l to 1.0 g/l.

8. A method according to claim 7, wherein the monofluorotrichloromethane is added in an amount of about 1.0 g/l.

9. A method according to claim 6, wherein the butanol is separated by solvent extraction using a fluorocarbon.

10. A method for producing butanol by fermentation which comprises culturing under anaerobic conditions *Clostridium acetobutylicum* having the identifying characteristics of A.T.C.C. No. 824 in a culture medium containing about 1.0 g/l of monochlorotrifluoromethane, and separating the butanol from the culture medium using monofluorotrichloromethane solvent extraction.

11. A method for stimulating the growth rate of a microorganism of *Clostridium acetobutylicum* (ATCC No. 824) by culturing under anaerobic conditions said microorganism in a culture medium containing from about 0.01 g/l to 10.0 g/l of a fluorocarbon selected from the group consisting of monofluorotrichloromethane, monofluorodichloromethane, monochlorodifluoromethane, dichlorodifluoromethane, dichlorotetrafluoroethane and mixtures thereof in an amount sufficient to stimulate the growth rate of said microorganism.

12. A method according to claim 11, wherein the fluorocarbon is monofluorotrichloromethane.

13. A method according to claim 15, wherein the monofluorotrichloromethane is added in an amount of about 0.2 g/l to 1.0 g/l.

14. A method according to claim 15, wherein the monofluorotrichloromethane is added in an amount of about 1.0 g/l.

* * * * *